United States Patent [19]

Wumpelmann et al.

[11] E Patent Number: Re. 33,441

[45] Reissued Date of Patent: Nov. 13, 1990

[54] IMMOBILIZATION OF BIOLOGICALLY ACTIVE MATERIAL WITH GLUTARALDEHYDE AND POLYAZAETIDINE

[75] Inventors: Mogens Wumpelmann, Herlev; Henrik Mollgaard, Lyngby, both of Denmark

[73] Assignee: Novo Industri A/S, Bagsvaerd, Denmark

[21] Appl. No.: 512,823

[22] Filed: Apr. 23, 1990

Related U.S. Patent Documents

Reissue of:

[64] Patent No.: 4,892,825
Issued: Jan. 9, 1990
Appl. No.: 213,773
Filed: Jun. 30, 1988

U.S. Applications:

[63] Continuation-in-part of Ser. No. 874,141, Jun. 13, 1986, abandoned.

[30] Foreign Application Priority Data

Jun. 14, 1985 [DK] Denmark ..... 2692/85
Jul. 1, 1987 [DK] Denmark ..... 3369/87

[51] Int. Cl.[5] ..... C12N 11/08; C12N 11/02; C12N 11/04

[52] U.S. Cl. ..... 435/180; 435/177; 435/182

[58] Field of Search ..... 435/94, 174, 177, 180, 435/182

[56] References Cited

U.S. PATENT DOCUMENTS

| | | | |
|---|---|---|---|
| 3,779,869 | 12/1973 | Zienty | 435/174 |
| 3,974,036 | 8/1976 | Snell | 435/174 |
| 3,980,521 | 9/1976 | Amotz et al. | 435/174 |
| 4,288,552 | 9/1981 | Gestrelius | 435/174 |
| 4,355,105 | 10/1982 | Lantero, Jr. | 435/94 |
| 4,436,813 | 3/1984 | Wood et al. | 435/180 X |
| 4,600,692 | 7/1986 | Wood et al. | 435/180 X |

*Primary Examiner*—David M. Naff
*Attorney, Agent, or Firm*—Morris Fidelman; Franklin D. Wolffe

[57] ABSTRACT

Immobilized biologically active material in particle form is prepared by cross-linking with glutaraldehyde and polyazetidine. An aqueous dispersion or solution of biologically active material is partially cross-linked with glutaraldehyde, a wet pasty mass is recovered by dewatering and the mass is sub-divided into discrete particles. A polyazetidine prepolymer is added before, at the beginning or subsequent to partially cross-linking but prior to subdividing the pasty mass into particles, and the prepolymer is allowed to cross-link.

18 Claims, No Drawings

IMMOBILIZATION OF BIOLOGICALLY ACTIVE MATERIAL WITH GLUTARALDEHYDE AND POLYAZAETIDINE

Matter enclosed in heavy brackets [ ] appears in the original patent but forms no part of this reissue specification; matter printed in italics indicates the additions made by reissue.

This application is a continuation in part of copending application Ser. No. 874,141 filed June 13, 1986, now abandoned.

This invention relates to a method for immobilizing biological materials by cross-linking with polyazetidine and, in a preferred mode, to a method for converting cell bound enzymes into cell mass enzyme particles.

BACKGROUND OF THE INVENTION

Immobilized enzyme products, especially immobilized enzyme products intended for use in a column has been a rapidly growing field as of the date hereof. Research efforts have been directed towards producing immobilized enzyme products of ever lower price, better physical strength, higher unit activity and of particle size and shapes giving rise to a minimum pressure drop during column operation as well as a high particle strength against abrasion. As of the date hereof, workers in the art have made available a substantial number of reasonably satisfactory methods to immobilize enzymes.

This invention is directed, in a preferred mode thereof, to the conversion of cell bound microbial enzymes into particle form immobilized enzymes made from the cell mass of the microorganism. The discussion of enzyme immobilization hereinafter provided is largely within a context of this type of immobilized enzyme product.

On the whole, as the art has advanced, product and method deficiencies, such as non-optimum particle size distribution, lack of control over particle shape and the cost factor of relatively low product yield, long considered to be unimportant defects in the immobilization process become major defects, which must be obviated. For example, glutaraldehyde has been employed in commercial practice for cross-linking cell bound enzymes according to the teachings of Amotz U.S. Pat. No. 3,980,521. Yet, glutaraldehyde is not an ideal cross-linking agent, for cell bound enzymes at least, reacting only with —$NH_2$ and —SH groups. The cells of many microorganism species react poorly with glutaraldehyde.

A polyazetidine prepolymer may be employed advantageously for cross-linking purposes, such being suggested by Wood et al. U.S. Pat. No. 4,436,813 and by "A Novel Method of Immobilization and Its Use in Aspartic Acid Production," Wood et al., Bio/Technology, December 1984, pp. 1081-1084. This Patent and Paper ar incorporated by reference herein. The polyazetidine prepolymer cross-linking system is more widely applicable to immobilization of cell bound enzymes than is glutaraldehyde because cross-linking reactions take place between the polyazetidine prepolymer and —COOH and —OH groups as well as —$NH_2$ and —SH groups.

The instances to which practice of this invention is directed in particular are those when the desired enzyme form constitutes particles made from the microorganism cells, and cellular substances, and cross-linking reagent(s), and optionally, auxiliary cross-linking agents, e.g., proteins and/or agglomerating agents, e.g., polyelectrolytes, and/or finely-divided filler materials. The particles are essentially homogeneous. Such enzyme product form are variously termed herein as cell mass particles and/or cell mass particulate form. It is noted parenthetically, that the process of above-referenced Wood et al. Patent and Paper is directed principally to immobilizing the enzymatically active microorganism cells and cellular substances on carrier particles, and that the inventors hereof strongly prefer the cell mass particle form over a carrier base particle form of immobilized enzyme product the latter not being essentially homogeneous particles.

Efforts by the inventors hereof to employ polyazetidine prepolymer cross-linking to generate cell mass particulate form enzyme products evidenced existence of material deficiencies to the process taught by the prior art. The reaction mixture constitutes an aqueous dispersion of the polyazetidine prepolymer in solution and individual microorganism cells along with any cellular substances present, or other biological material necessitating conduct of the curing reaction en mass. By crushing the reaction product and sieving, a desired particle size fraction may be recovered, but overall the yield of the wanted particle size fraction is usually low, and also, the shape of the individual particles is not controlled. Thus, cross-linking a non-particulate cell mass composition gives rise to immobilized enzyme product wherein particle shape and size is not controlled.

Although the foregoing discussion of the background of the invention and the description of the invention which now follows is couched in terms of cell bound enzymes and a cell mass particulate product, such is done to facilitate understanding of the invention and to describe preferred practice of the invention in fulsome fashion. It is emphasized that practice of the invention is applicable to biological materials more generally, including notably, homogenized cell sludge, enzymes in solution (e.g., extra cellular enzymes), co-enzymes and anti-bodies.

OBJECT OF THE INVENTION

The object of the invention is the provision of a method adapted to produce a particulate form of biological material in high yield, of particles with high physical strength, whereby also the shape and size of the particles can be controlled.

Enzymes, soluble and cell bound alike, are preferred biological materials and cell mass immobilized enzyme products are particularly preferred products of the invention.

Enzymes of particular interest to the inventors hereof are glucose isomerase, penicillin acylase and nitrilase.

STATEMENT OF THE INVENTION

In brief, the method of this invention comprises partially cross-linking enzymatically active microorganism cells or some other biological material in aqueous solution or suspension through reaction with glutaraldehyde, followed by dewatering of the resulting flocculated solids, resulting in a pasty consistency mass of a (consistency) and coherency suitable for particle shaping. Then, (wet) particles of desired shape and size are generated from the mixture followed by drying. The polyazetidine prepolymer solution is incorporated before or after dewatering, more preferably the former. Curing of the polyazetidine prepolymer which occurs during the drying step, converts the pasty mass particles into cured particles of high physical strength.

Immobilized enzyme products prepared according to the invention employed in packed bed exhibit a very small pressure drop (e.g., a pressure drop which is only around 50% of a comparable prior art product) and a high physical strength and resistance against abrasion, and moreover, the immobilized enzyme products are relatively inexpensive to make due to the high yield of usable particles. Also, it has been found that preferred embodiment immobilized enzyme product prepared according to the invention exhibit a high volumetric activity.

DETAILED DESCRIPTION OF THE INVENTION

The cross-linking reactions between enzymatically active cellular substances and a polyazetidine prepolymer to crosslink the enzyme into a composition capable of repeated use is taught by the above-referenced U.S. Pat. No. 4,436,813 and Paper of Wood et al., (see also G. J. Carlton et al, Biotechnology, vol. 4, pp. 317-320 (1986)) and, therefore, need not be discussed in detail here.

The polyazetidine polymer used for the practice of this invention may be any water-soluble polymer with a substantial content of reactive azetidine rings, such as those prepared by reacting a polyamide with epichlorohydrin according to German patent publication No. DT-AS-1,177,8254. Examples of commercially available products are Polycup 2002, Kymene 557H and Reten 304 (these are all trade marks of Hercules Inc., U.S.A.).

A representative polyazetidine prepolymer in aqueous solution, such as is depicted below, e.g., Polycup 172 (Hercules, Inc.).

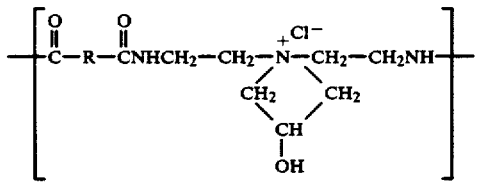

where R is typically $\text{+}CH_2\text{+}_x$ is cross-linked by heat, $H_2O$ removal or pH adjustment to an alkaline pH value. Some of the curing reactions are reaction of the prepolymer with available $—NH_2$, —OH, —SH, —COOH groups of cellular substances on or from the enzymatically active microorganism cell.

Unless the reaction mass is sub-divided into individual particles prior to curing a cross-linked cell mass product will be a single block of material, i.e., a coherent mass that must then be sub-divided into the desired particle from enzyme product. As has already been pointed out, such a conversion results in relatively low yield of the desired size range particles and, in addition, the shape of the individual particles is not controlled at all.

Forming the cell mass into discrete particles prior to cross-linking of the polyazetidine prepolymer, would, of course, be desirable. Unfortunately, the fluid aqueous mixture of polyazetidine prepolymer and cell mass, e.g., cell sludge, is not well adapted to being formed into coherent particles.

As has been pointed out, the improvement of this invention is directed to conversion of a biological material such as microorganism cells into a wet past mass followed by subsequent subdivision of the mass into discrete particles. The present process can be considered to be a pretreatment procedure that is carried out prior to curing the polyazetidine. Subsequently, as the particles dry, the polyazetidine cross-linking reactions take place and the particles assume their ultimate coherency, hardness etc. Conversion, e.g., of the microorganism cells, into a relatively coherent pasty mass is accomplished by carrying out partial cross-linking of the biological material in aqueous dispersion by reaction with glutaraldehyde, followed by dewatering.

Biological materials that can be immobilized by the method of this invention include enzymes soluble or cell bound alike, microorganism cell (intact or disrupted cells, viable or non-viable), antibodies and coenzymes. The biological material to be immobilized should be in an aqueous solution or dispersion and may have been purified as desired by conventional techniques. The degree of purification is not critical to the practice of the invention.

It has been found that the quantity of water present in the (pretreatment) partial cross-linking reaction mixture of this invention is not critical. Excess water will be removed from the flocculated partially cross-linked solid phase substance in the reaction product mixture during dewatering without any serious loss of active material. Thus, water may be added to the solution or dispersion of the biological material to obtain a convenient consistency for the partial cross-linking reaction, then excess water is removed by dewatering. The term dewatering is employed herein within a context of physical removal of water, such as, for example, decanting, filtration, centrifugation and the like.

A convenient preferred starting material for practice of this invention is the enzymatically active cell sludge recovered from a fermenter through filtering or centrifuging the culture broth. The cell sludge may be used as such or first be homogenized. Since the fermenter may not be in close proximity to the immobilization facility, it is noted that the optionally homogenized cell sludge may be stored in frozen state. Indeed, freezing, then thawing of the cell sludge maybe advantageous rather than be an activity losing detriment in the overall process sequence.

The detailed chemistry of the reactions involved in partial cross-linking through reaction of the microorganism cells and cellular substances with glutaraldehyde are not known to the inventors hereof. Indeed, insofar as the inventors hereof are aware, the chemistry of cross-linking with glutaraldehyde is not fully elucidated. Reference is made to Douglas J. Ford, 2. Reaction of Glutaraldehyde with Proteins, University of Cincinnati; and Hardy, The Nature of the Cross-linking of Proteins by Glutaraldehyde, Part I, Journal of the Chemical Society, Perkin Transactions, Vol. 1, Pg. 958, 1976. However, the art is familiar with practical results from reacting glutaraldehyde with microorganism cells.

Glutaraldehyde has been suggested to the enzyme art for cross-linking to generate cell mass particle form enzymes, as witness the teachings in the aforementioned U.S. Pat. No. 3,980,521. Glutaraldehyde has also been suggested for stabilizing cell bound enzymes on the microorganism cells as witness the teachings in U.S.

Pat. No. 3,779,869. The usage of glutaraldehyde in practice of this invention is related to the teachings of both above-referenced patents, yet is quite different therefrom. Although occurrence of cross-linking reactions is desired, in large measure the exact extent to which reaction with glutaraldehyde prevents loss of enzyme from individual microorganism cells (see U.S. Pat. No. 3,779,869), or can convert cells and cell fragments into a coherent covalently linked matrix (see U.S. Pat. No. 3,980,521), is not material for practice of this invention.

The purposes of treatment with glutaraldehyde in practice of this invention is generation of a reaction product mixture that contain flocculated solids which then can be dewatered and so doing generates a pasty mass adapted for subdivision into discrete particles. The pasty mass is capable of admixture with an aqueous polyazetidine prepolymer and then be a mixture of a coherent consistency from which particles may be formed. Generation of the particle forming capability is the objective sought. It should be appreciated that the term "pasty mass" as employed herein is both descriptive of the partially cross-linked (still wet) dewatered product and connotes existence of cohesiveness and a particle forming capability.

Incident to treatment of a cell sludge or other biologic material with glutaraldehyde, auxiliary cross-linking agents containing —$NH_2$ groups may be added to the reaction mixture e.g., polyethylene imine, chitosan, albumine, gelatine. Also, flocculating agents may be added. Further, it may be advantageous to treat the cell sludge with a metal ion complexing agent such as EDTA. The exemplary details hereinafter provided about preferred embodiments of this invention are not likely to be applicable in all their detail to other cell bound enzymes. Cut and try tests within the preferred glutaraldehyde ranges are suggested to ascertain whether inclusion of auxiliary cross-linking agents and/or inclusion of polymeric flocculating agents is advisable, or, perhaps, is necessary to achieve a workable consistency and the proper water content in the dewatering partially cross-linked cell mass.

It may be noted also that finely divided filler materials and/or enzyme stabilizers (e.g., metal ions) when presence of such is desired in the ultimate cell mass immobilized enzyme product may best be incorporated into the cell mass incident to the partial cross-linking with glutaraldehyde.

It has been found that the quantity of water in the cell sludge and that added with the glutaraldehyde and with any optional agent in the partial cross-linking reaction mixture such as flocculating agent, auxiliary cross-linking agent, enzyme stabilizer ions, etc. is not a critical factor. All water in excess will be filtered or centrifuged off from the partially cross-linked pasty mass. However, the relative proportions of cell sludge dry matter and glutaraldehyde are important.

According to one preferred mode of the invention, the polyazetidine prepolymer solution is incorporated into the pasty mass.

In such preferred embodiment of the method according to the invention, the amount of glutaraldehyde is between 5% and 40% w/w in regard to cell sludge dry matter, preferably between 10% and 20% w/w. If the amount of glutaraldehyde is below 5% w/w, the filterability of the partially cross-linked cell mass may be inferior, and if the amount of glutaraldehyde is above 40% w/w, the enzyme yield recovery in the immobilized enzyme product maybe unsatisfactory.

The dewatered partially cross-linked cell mass has a water content of 70–90% w/w, preferably 80–85% w/w. If the water content is less than 70% w/w, the pressure drop characteristics of the particulate immobilized enzyme product may not be satisfactory, and if the water content is above 90% w/w, performance of the particle shaping step may be unsatisfactory. Thus, the relatively narrow 70%–90% water content in the dewatered cell mass is relatively critical in practice of the invention.

The practitioner of this invention will soon recognize the most workable consistency area. The particle forming capability is somewhat poor at both ends of the 70–90% water content range. It is noted that water content for the most workable consistency will vary enzyme to enzyme.

The water content range provided above for the dewatered partially cross-linked cell mass takes into account that the polyazetidine prepolymer added will be as an aqueous solution of 10–15% solids. The preferred range of 80–85% water virtually assumes about a 12% polyazetidine prepolymer solution and the more preferred polyazetidine prepolymer content in regard to the dry weight of the cells will be employed.

The polyazetidine prepolymer is added in an amount of between 5% and 30% w/w (dry matter basis), more preferably 10–20% w/w (dry matter basis) in regard to the cell sludge. If the amount is below 55% w/w, the pressure drop reduction improvement obtained in the particulate product is unsatisfactorily low, and if the amount is above 30% w/w the enzyme yield in the immobilized enzyme particulate product is unsatisfactorily low. Thus, should a particular cell-bound enzyme require less than 10% or more than 20% of the polyazetedine prepolymer for yield or product stability reasons, arbitrary adoption of the above given most preferred 80–85% water content range is not advised.

It is to be understood that the foregoing discussion of proportions is within a context of incorporating the polyazetidine prepolymer solution into a partially cross-linked pasty mass. Such has not been found to be necessary, and a more preferred mode is to add the polyazetidine prior to dewatering, at all of which times the aqueous solution or dispersion of the biological material is still in fluid state.

Although, according to this mode of the invention, the polyazetidine prepolymer solution is added prior to dewatering, it has been found that very little of the polyazetidine is lost during dewatering. Apparently polyazetidine binds to the biological material, e.g., to enzymatically active microorganism cells, by acting as a cationic flocculent, or the polyazetidine can be made to bind to the material through selection of appropriate flocculent(s). In any event, the need for a flocculent as well as a suitable type and quantity of flocculent is readily determined by those skilled in the art for whatever particular enzyme or other biological material is being cross-linked. Thus, optionally but desirably, a flocculent is also added while the fluid state exists.

Aside from a requirement for a lesser amount of polyazetidine for optimum product properties when polyazetedine prepolymer is added before the dewatering step, the process remains the same. The processing conditions for partial cross-linking with glutaraldehyde already described apply, as for example temperature 0°–60° C., pH 5–9, buffer as needed, cross-linking for 5–60 minutes, auxiliary crosslinking agents when advisable or when desired (to dilute the enzyme for instance).

The auxiliary cross-linking agents may be present in quantities of up to 100% of the biological material by weight dry matter, preferably much less, depending on the auxiliary agent, notably 20% or less for polyethylene imine, 50% or less for albumin or gelatine and 10% or less for carboxymethyl cellulose. Inclusion of flocculant as appropriate.

The great advantage of incorporating the polyazetidine prepolymer into the pre-dewatered and still fluid mixture is reduction in the proportion of polyazatidine required and for better control over the properties of the filter cake and of immobilized enzyme product.

Thus, a relatively high proportion of polyazetidine in the product generally yields physically strong particles, whereas a lower proportion yields particles with lower diffusion restriction and therefore with higher activity. The most suitable amount of polyazetidine for this mode of the invention will usually be in the range about 0.1–about 10% by weight of total dry matter in the solution or dispersion, typically about 0.5–5%, e.g., preferably about 0.5 to 3%.

In both modes of the invention discussed above, the partially cross-linked dewatered mixture is a pasty mass that exhibits a coherency and a consistency suited to particle shaping. A preferred particle shaping technique is to extrude the dewatered mixture, then partially dry (drying cures the polyazetidine prepolymer), thereafter spheronize, followed by supplementary drying, the last being optional. The marumerizing practice of Great Britain No. 1,362,265 may be followed.

Partially cross-linking the suspended biological material particles changes their physical character, makes them sticky so that upon dewatering of the two phase aqueous mixture the solids fuse into a relatively coherent pasty mass. Comparably. partially cross-linking a dissolved biological material, such as for example enzyme in solution, causes precipitation of the biological material. Upon dewatering of the two phase aqueous mixture, the precipitate converts into a relatively coherent pasty mass. Thus, in each event, dewatering, e.g., by filtration, removes much of the water phase generating the desired pasty mass. Prior to dewatering the precipitated solids or the partially cross-linked particles which even collect in bunches, i.e., become flocculated. Inclusion of flocculant is to improve flocculation of the partially cross-linked solid phase. Flocculants, when present and polyazetedine prepolymer, when present, are mostly in the pasty mass.

To repeat the pasty mass made according to practice of this invention exhibits a significant level of coherency, allowing the mass to be subdivided, e.g., extruded, and the extrudate ribbons do not fuse together before curing of the polyazetidine prepolymer has been effected.

Additional water is removed during the curing step, e.g., by evaporation as the cross-linking reaction proceeds, so that a physically strong relatively dry product is obtained. Preferred techniques are air drying or fluidized-bed drying, generally at 15°–80° C. In case of very sensitive biological materials, low temperature drying or freeze-drying may be needed.

The pasty mass is a homogeneous mixture. Any particulate matter therein, e.g., finely, divided filler particles, is uniformly dispersed. The composition of any one portion of the pasty mass will be no different from any other portion. Such uniformity carries through to the product particles. Each will have the same composition. Also, the center of each particle is of the same composition as the particle periphery. In this sense, the product particles are essentially homogeneous.

In all preferred embodiments of the method according to the invention, the particle form immobilized enzyme is dried to a water content of about 15–25% w/w. With an ultimate water content of above around 25% the microbial stability of the product is unsatisfactory. Furthermore, as previously indicated, with water content above around 25% the cross-linking with the polyazetidine prepolymer may not have taken place or may not be complete; the particles may tend to aggregate over time in storage. Drying to a water content of below about 15% may cause loss in enzyme activity.

UTILITY

The process of this invention is widely applicable to immobilization of biological materials, such as enzymes, particularly, glucose isomerase, penicillin acylase and nitrilase, cell mass, coenzymes and antibodies (monoclonal or polyclonal).

Enzymes which may be immobilized can be in the form of enzymatically active cells, or partly or fully homogenized cell paste, or as a largely cell-free enzyme solution. Some instances where the method of the invention is particularly advantageous are:

glucose isomerases from Streotomcyes sp.. e.g. from the following species:

| |
|---|
| *S. murinus* |
| (EP 0 194 760) |
| *S. flavovirens* |
| *S. achromogenus* |
| *S. echinatus* |
| *S. wedmorensis* |
| *S. albus* |
| (U.S. Pat. No. 3,616,221) |
| *S. olivochromogenes* |
| *S. venexueloe* |
| (U.S. Pat. No. 3,622,463) |
| *S. griseoflavus* |
| (U.S. Pat No. 4,137,126) |
| *S. galbus* |
| *S. gracilis* |
| *S. margensis* |
| *S. niveus* |
| *S. plantensis* |
| (Hungarian patent 12,415) |
| *S. violaceoniger* |
| (German patent 2,417,642) |
| *S. acidodurans* |
| (U.S. Pat. No. 4,399,222) |
| *S. phaeochromogenes* |
| *S. fradiae* |
| *S. roseochromogenes* |
| *S. olivoceus* |
| *S. californicus* |
| *S. vanoceus* |
| *S. virginioe* |
| (Japanese patent publication 69-28,473) |
| *S. olivaceus* |
| (U.S. Pat. No. 3,625,828) |

glucose isomerase from Bacillus coagulans. (see U.S. Pat. No. 3,979,261).

glucose isomerase from Actinoplanes sp., especially A. missouriensis.

glucoamylase from Asperoillus sp., especially from black Aspergilli and more especially from A. niger (see U.S. Pat. No. 3,677,902), or from Rhizoous sp.. especially Rh. delemar or Rh. niveus.

penicillin-V acylse from Fusarium sp., especially F. uioides, F. aroiilaceum, F. avenaceum, F. bulbioenum, F. coeruleum, F. eouiseti, F. lateritium, F. minimum, F.

monoliforme, F. oxysporum, F. sambucinum, F. semisectum, F. solani, and F. sulphureum (see GB No. 891,173).

penicillin acylase from Eschericia coli, Proteus rettoeri, Kluyvera citrophila, Bacillus sohaericus. Bovista plumbea or Bacillus megaterium.

lactase from Kluyveromyces sp., especially from K. fragilis or K. lactis.

cyanide hydratase according to Danish DK No. 87/1283 nitrilase, nitrile hydratase or amidase, especially from Rhodococcus sp., pseudomonas sp. or Brevibacterium sp.

See U.S. Pat. No. 4,001,081, EP Nos. 0 093 782 and 0 188 316.

The cell mass immobilized into cell mass particle form by the process of the invention may be viable. or non-viable intact cells as well as in the form of homogenized cell paste. The cells are preferably of microbial or plant orgin. Some preferred examples follow:

viable cells for use in bioconversion, e.g., yeast for ethanol fermentation.

cells with enzymatic activity, e.g., fungal mycelium containing cyanide hydratase, see EP Nos. 0 061 249 and 0 116 423.

cell mass preparations for use in adsorptive removal, e.g., of heavy metals, see EP No. 0 181 497, U.S. Pat. Nos. 4,320,093, 4,298,334, 4,293,333 and JP-A No. 49-104,454.

EXEMPLARY APPLICATIONS OF THE INVENTION

As has already been pointed out, a preferred mode of this invention is directed to instances when the art desires to convert cell bound enzymes into a cell mass particle form. Within the above-described parameters for practice of this invention is sufficient variability to make practice of the invention applicable to any microorganism source cell bound enzyme. For example, glucose isomerase a well known cell bound enzyme, has been produced on a large scale cultivation of Bacillus coagulans. An excellent glucose isomerase is elaborated by glucose isomerase producing strain belonging to the genus Streotomcyes, e.g., a Streotomcyes murinus cluster strain. The cell bound enzyme from Bacillus coaoulans can be immobilized readily by reaction with glutaraldehyde; see the aforementioned U.S. Pat. No. 3,980,521. However, the cell bound enzyme produced by strains of the genus Streptomyces, including notably the Streptomyces murinus cluster is characterized by an insufficient cross-linking capability with glutaraldehyde to produce a satisfactory cell mass particle form immobilized enzyme. However, either of these cell bound enzymes may be immobilized in cell mass particle form through practice of this invention. It follows, of course, that practice of this invention is particularly suited to the Streptomyces murinus enzyme. Glucose isomerase is a commercially important enzyme, which is to say, that immobilization of the Streptomyces murinus glucose isomerase is one preferred mode practice of this invention.

The widespread applicability of this invention is also exemplified hereinafter by a disparate commercially important cell bound enzyme, i.e., trytophan synthetase derived from a strain of E. coli. Preparation of this enzyme, too, is a preferred mode practice of the invention. None of the prior art immobilization methods investigated by the inventors hereof resulted in an immobilized tryptophan synthetase product of satisfactory physical strength. It is noted that tryptophan synthetase requires a cofactor. Such is present in the cytoplasm. Since disruption of the cell would cause loss of the cofactor, immobilization of whole cells is employed in the instance of the tryptophan synthetase enzyme.

Enzyme granules made according to practice of this invention, particularly according to preferred practices of the invention, exhibit superior physical properties. In packed bed they exhibited a pressure drop for the liquid flowing therethrough which is only around 50% of a comparable prior art product. (In this test study, the comparable prior art product was a glutaraldehyde cross-linked Bacillus coaoulans glucose isomerase made according to the teachings of U.S. Pat. No. 3,980,521, a product that is in widespread commercial usage.) In addition, high physical strength and resistance against abrasion were found.

For further understanding of the practice of this mode of the invention, the following specific Examples are presented.

EXAMPLE 1

Glucose isomerase containing cells of Streptomyces murinus, DSM 3252 were cultivated in a conventional medium comprising glucose, a complex nitrogen source, minerals and trace elements.

After pH adjustment of 7.0–7.5 the cells were recovered from the fermentation broth by centrifugation and homogenized after addition of $MgSO_4$, $7H_2O$ in an amount of 0.5% w/v by means of a Manton-Goulin homogenizer. The homogenized cell sludge was kept in −18° C. and thawed immediately before use in a immobilization experiment.

300 g of homogenized cell sludge with a dry matter content of 6.7% was diluted to 750 ml with 1.5% $MgSO_4$, $7H_2O$, and pH was adjusted to 7.5. 30 g Corcat p-18 polyethylene imine flocculent (Cordova Chem. Co.) was added. Then 9.24 g of 50% glutaraldehyde was added; pH was maintained at 7.4–7.6 for one hour. The flocs were collected by filtration.

The filter cake containing approximately 15.8% DM was divided into two equal parts in terms of dry matter content. The two parts were mixed with 0 and 15% w/w (dry matter basis) respectively of Polycup ® 1884 polyazetidine prepolymer solution, pH 7.5 (from Hercules, Inc., Delaware) calculated on filter cake dry matter. Both parts were extruded through 0.8 mm orifices. The extruded material was allowed to dry at room temperature to a dry matter content of 83–85% w/w. The 300–700 u fraction was obtained by sieve fractionation.

The glucose isomerase activity (measured according to NOVO Document F 850399) recovered in the two immobilized enzyme preparations was approximately the same. Pressure drop (in g/cm2) measured according to NOVO, AF 166 is given in the following Table 1.

TABLE 1

Pressure drop versus percentage of polyazetidine, calculated as dry matter on filter cake dry matter.

| % polyazetidine | 0 | 15 |
|---|---|---|
| Pressure Drop (25 h/50 h) | 14/17 | 6/7 |

EXAMPLE 2

A tryptophan synthetase producing strain of E. coli, ATCC 15491, was grown on an agar slant at 37° C. and from there transferred to a preculture in shake flasks at 37° C. The preculture was inoculated on a medium prepared as follows. The composition of the medium was:

| | |
|---|---|
| $(NH_4)_2SO_4$ | 8 g/l |
| $KH_7PO_4$ | 1.6 g/l |
| $Na_2HPO_4.2H_2O$ | 5.6 g/l |
| Trisodiumcitrate, $2H_2O$ | 0.5 g/l |
| NaCl | 3 g/l |
| $MgSO_4.7H_2O$ | 0.5 g/l |
| $CaCl_2.2H_2O$ | 00.2 g/l |
| $FeCl_32H_2O$ | 90 mg/l |
| $ZnSO_4.7H_2O$ | 20 mg/l |
| $MgSO_4.4H_2O$ | 24 mg/l |
| $MnSO_4.4H_2O$ | 22 mg/l |
| $CuSO_4.5H_2O$ | 4 mg/l |
| KI | 4 mg/l |
| $NaMoO_4.2H_2O$ | 4 mg/l |
| $H_3BO_3.6H_2O$ | 1.2 mg/l |
| $CoCl_2.6H_2O$ | 6 mg/l |
| $NiCl_2.6H_2O$ | 6 mg/l |
| *Biotin | 4 μg/l |
| *Calcium pantothenate | 800 μg/l |
| *Folic acid | 4 μg/l |
| *Inositol | 4000 μg/l |
| *Niacin | 800 μg/l |
| *p-aminobenzoic acid | 400 μg/l |
| *Pyridoxine HCl | 800 μg/l |
| *Riboflavin | 400 μg/l |
| *Thiamine HCl | 800 μg/l |

The medium was sterilized at 121° C. for 25 minutes except for the vitamins (*), which were added by sterile filtration after cooling together with dextrose (10 g/l) and indole in 48% ethanol (125 mg/l). The submerged fermentation was conducted under aseptic conditions at 37° C. with aeration at 1 volume/volume/minute, agitation at 500 rpm and pH controlled by acid/base addition at pH 7.0 for 40 hours. 24 hours after inoculation a further addition of dextrose (40 g/l) and indole in 48% ethanol (875 mg/l) was carried out. Cells were harvested after 40 hours by centrifugation and immediately used for the immobilization experiments described as Example 3 hereinafter.

EXAMPLE 3

60 g of wet cells recovered as described in Example 2, having a dry matter content of 17% w/w were resuspended in 1200 ml of 0.2M EDTA (adjusted to pH 7.5) and left for 30 min at room temperature and then centrifuged. The aqueous EDTA washing procedure was repeated once.

The wet cells were mixed with 300 of 85 mM $KH_2P_4$, pH 7.5; 8.4 g of polystyrene from Kodak (200–400 mesh, cross-linked with 2% w/w divinylbenzoic acid), 96 mg of pyridoxal phosphate and 9.6 g of a 12.5 w/v glutaraldehyde solution. The pH value was maintained at 7.5 by addition of base throughout the immobilization procedure. Then 60 g of Corcat P-150 polyethylene imine solution from Cordova Chemical Company of Michigan, adjusted to pH 7.5 with 10N NaOH, was added, followed by the same amount of glutaraldehyde solution as before. Dilution was carried out with 900 ml of 50 mM $KH_2PO_4$, pH 7.5 after 1 hour from the first addition of glutaraldehyde. Then flocculation was performed by addition of 250 ml of 1% w/v Superloc A 130 from American Cyanamide. Partially cross-linked and flocculated cells were recovered by filtration. The filter cake containing approximately 19% w/w of dry matter was divided into two equal parts. One part was mixed with 7.2 g of Polycup® 172 (Hercules, Inc., Delaware) pH 7.5, corresponding to 16.5% w/w of dry polyazetidine prepolymer in regard to the dry matter in the wet cells recovered by centrifugation from the fermentation.

Both parts were extruded through 0.8 mm holes.

The extruded material (both parts) was allowed to dry at room temperature to a dry matter content of 90% w/w. The 300–700 um fraction was obtained by sieve fractionation.

The tryptophan synthetase activity recovered in the two immobilized enzyme product was approximately the same. The pressure drop (in g/cm2) measured according to NOVO AF 166 of the product with polyazetidine wa 14(25 h)/15 (50 h) and of the product without polyazetidine 23 (25 h)/24 (50 h).

The examples which now follow are directed to the more preferred mode of the invention wherein the polyazetidine prepolymer is added prior to dewatering, including being present during the partial cross-linking treatment. All other (dry substance) ingredients also are present in the pretreatment reaction mixture.

It may now be appreciated better that the underlying rationale to this more preferred mode of practice of this invention is to achieve conversion of an enzyme (or other biologic material) in aqueous solution or uniform dispersion together with any other dissolved or dispersed ingredients into a two phase mixture wherein desirably the (partially cross-linked) solid phase will contain all of the (dry basis) substances desired in the final product and the aqueous phase nothing but water and undesired ions, etc. Dewatering converts the solid phase substances into a pasty mass for forming into coherent particles. Thus, flocculants, auxiliary cross-linking agent and other optional ingredients are added to the aqueous solution or dispersion when their presence facilitates generation of a more suitable two phase dewaterable inhomogeneous mixture.

The examples which follow exemplify most preferred practice of the invention and in addition illustrate the effect of varying the ingredients in the (partial crossinking) reaction mixture so as to be suggestions to those skilled in the art how best to approach immobilizing some biological material not exemplified herein.

EXAMPLE 4

Glucose isomerase containing cells were produced by fermentation of Streptomyces murinus, strain DSM 3253, according to Example 1.

The cells were harvested by centrifugation of the culture broth. The cell sludge had a dry substance content of 7.0%.

The general immobilization procedure was as follows; To 300 g cell sludge was added 300 g deionized water containing 1.5% $MgSO_4$, $7H_2O$. pH was adjusted to 7.5. The indicated amount of polyethyleneimine (Sedipur, product of BASF, West Germany) was added, and after thorough mixing the mixture was cross-linked by addition of 15% active glutaraldehyde based on cell sludge dry substance plus polyethyleneimine dry substance. After 1 hour the polyazetidine prepolymer (Polycup ®2002) was added and thoroughly mixed with the cross-linked cell suspension.

The mixture was then flocculated by addition of a cationic flocculent, Superfloc C521 (Cyanamid Int.). The cross-linked enzyme was recovered by filtration, formed into particles by extrusion through a 0.8 mm screen and dried at room temperature.

The glucose isomerase activity was measured by NOVO analysis method F-855310 (available on request from Novo Industri A/S, Denmark) and the physical stability determined as pressure drop over a column.

The pressure drop was measured over a column with a diameter of 24 mm and an enzyme bed height of 4 cm (5 g enzyme). The solution, 45% glucose in demineralized water with 1 g $MgSO_4S/1$, was pumped through the column at a rate of 40 g/min at 60° C. The pressure drop (in mm of liquid) describes the physical stability of the enzyme particle, i.e., a low pressure drop corresponds to a good physical stability. The results are shown in the table below.

| | | Glucose isomerase activity (μmol/min/g) | Pressure drop (mm) |
|---|---|---|---|
| 5% polyethyleneimine | 0% polyazetidine | 614 | 400 |
| | 2.5% polyazetidine | 667 | 99 |
| | 5% polyazetidine | 586 | 57 |
| 10% polyethyleneimine | 0% polyazetidine | 692 | 105 |
| | 2.5% polyazetidine | 578 | 11 |
| | 5% polyazetidine | 506 | 10 |

Preparations with pressure drops exceeding about 20 mm liquid are not considered to be well suited to industrial glucose isomerase columns. Activity decreases slightly with increasing polyazetidine concentration., This example clearly shows the improvement of physical stability of the immobilized preparations obtained with polyazetidine.

EXAMPLE 5

A similar experiment to that described in Example 4 was performed using a higher yielding descendant of DSM 3253.

The dry substance content of the cell sludge was 5.3%, and the cells were partially disrupted by homogenization. Otherwise the immobilization was performed as described in Example 4.

The results are given in the Table below.

| | | Glucose isomerase activity (μmol/min/g) | Pressure drop (mm) |
|---|---|---|---|
| 5% polyethyleneimine | 0% polyazetidine | 556 | 16 |
| | 1% polyazetidine | 855 | 13 |
| | 2.5% polyazetidine | 839 | 13 |
| | 5% polyazetidine | 707 | 8 |
| 10% polyethyleneimine | 0% polyazetidine | 651 | 12 |
| | 1% polyazetidine | 975 | 10 |
| | 2.5% polyazetidine | 911 | 5 |
| | 5% polyazetidine | 853 | 3 |

From these experiments, it can be concluded that the polyazetidine improves the physical stability of even very physically stable formation.

EXAMPLE 6

Bacillus coagulans containing glucose isomerase was immobilized with and without polyazetidine.

Homogenized cell paste of B. coaoulans prepared according to U.S. Pat. No. 3,979,261 was suspended in 0.1% $MgSO_4$ to a final dry substance concentration of 3%. Glutaraldehyde was added to a final concentration of 0.5%. After 60 min with mixing at room temperature polyazetidine prepolymer (Polycup ® 2002) wa added followed by floccillation with Superfloc C521. The cross-linked enzyme was recovered by filtration, formed into particles by extrusion and dried at room temperature.

Activity and pressure drop were measured as described in Example 1. Resistance to grinding was measured as turbidity (optical density) at 600 nm after 1 hour of vigorous stirring of 0.5 g enzyme in 20 ml 50 mM phosphate, pH 7 with a propeller. Before the assay the enzyme product had been swelled and washed in 6% NaCl in 50 mM phosphate, pH 7.0.

| Amount of polyazetidine (% dry substance) | 0 | 1 | 3 |
|---|---|---|---|
| activity (μmole/min/g) | 540 | 506 | 493 |
| pressure drop (mm liquid) | 5 | 3 | 2 |
| 25 grinding | 0.111 | 0.068 | 0.062 |

Both resistance to grinding and physical stability were improved by adding polyazetidine, while only a small activity loss was observed.

EXAMPLE 7

To exemplify immobilization of a soluble enzyme the amyloglucosidase from Aspergillus niger has been chosen. This enzyme is extracellular.

A commercial preparation AMG 400 L HP (Novo Industri A/S, Denmark) was dialyzed against 50 mM phosphate pH 7.0. The preparation was diluted to a dry substance concentration of 2% w/v, and an equal ammount of egg albumen was added (i.e., 2% w/v). Glutaraldehyde was added to a concentration of 0.6% w/v. After one hour of stirring, polyazetidine prepolymer (Polycup$^R$ 2002) was added to a final concentration of 0.08% w/v, and the mixture was flocculated with Filtrafloc (Servo B.V., Netherlands). Enzyme was recovered as described in previous examples.

Activity was measured as described in Novo Analysis Method AF159/2. Pressure drop was measured as described in Example 1, but at 35° and with 11% w/w glucose in 50 mM phosphate, pH 7.5.

| polyazetidine, % w/v | 0 | 0.08 |
|---|---|---|
| activity (μmol/min/g)* | 196 | 160 |
| 20 pressure drop (mm liquid) | 9 | 6 |

*Particle fraction: 425–710 μm

EXAMPLE 8

Cell paste of Fusarium sp. containing penicillin acylase activity (prepared according to British patent specification No. GB 891,173), which had been washed thoroughly with 0.9% NaCl, was suspended in 50 mM phosphate pH 7.0 to give a final dry substance content of 3%. Polyethyleneimine (Sedipur) was added to give a final dry substance content of 0.1% Glutaraldehyde was added to a final concentration of 0.2% w/v. After one hour with thorough mixing polyazetidine prepolymer was added, and finally the mixture was flocculated with a cationic flocculent Filtrafloc. The cross-linked enzyme was recovered by filtration, formed into particles by extrusion through a 0.6 mm screen and dried at room temperature.

Enzyme activity was measured by Novo analysis AF186, and the physical stability determined as pressure drop and resistance to grinding (see Example 6).

| Polyazetidine type | None | Polycup ® 2002 | | Kymene ® 557H |
|---|---|---|---|---|
| Polyazetidine (%) | 0 | 1 | 3 | 1 |
| activity* (PVU/g) | 72 | 57 | 42 | 35 |
| 10 pressure drop (mm liquid) | 6 | 4 | 3 | 2 |
| grinding | 0.563 | 0.305 | 0.140 | 0.103 |

*450–710 μm fraction

As can be seen from the above Table polyazetidine increases physical stability, i.e., gives increased resistance to grinding and gives highly improved pressure stability. However, this improvement is obtained at the expense of an activity loss which partly is due to diffusion limitation, which again is believed to be due to a more dense preparation when polyazetidine is present.

EXAMPLE 9

Fusarium sp. was immobilized as described in Example 5, but at different pH-values and with 1% Kymene ® 557H in all preparations.

Results are seen in the table below:

| pH | 6 | 7 | 8 |
|---|---|---|---|
| 25 activity (PVU/g) | 33.3 | 36.1 | 41.5 |
| pressure drop (mm liquid) | 2 | 3 | 3 |
| grinding | 0.171 | 0.154 | 0.188 |

The physical stability is good and independent of pH in the tested range (6–8).

EXAMPLE 10

The significance of time of polyazetidine prepolymer addition was examined with cell paste of Fusarium sp. Immobilization was done as explained in Example 5, but without PEI and with polyazetidine prepolymer (Polycup ® 2002) addition to a final concentration of 0.3% both before and after the addition of glutaraldehyde.

| Time for polyazetidine addition | not added | before glutaraldehyde | after glutaraldehyde |
|---|---|---|---|
| activity (PVU/g) | 58 | 32 | 31 |
| 10 pressure drop (mm liquid) | 27 | 6 | 4 |

The physical stability is increased both when polyazetidine is added before and after the glutaraldehyde.

EXAMPLE 11

Cell sludge of Rhodococcus erythropolis having ability to hydroyze nitrile (prepared according to EP No. 188,316) was diluted to 2% dry substance with water. 10% polyethyleneimine (Sedipur) (based on dry substance of cell sludge) was added, and pH was adjusted to 7.0. The mixture was cross-linked by addition of 5% active glutaraldehyde (based on cell sludge dry substance plus polyethyleneimine dry substance). After 1 hour, 2% of polyacetidine prepolymer (Kymene) (based on total dry substance) was added.

The mixture was then flocculated by addition of an anionic flocculent, Superloc A 130. The cross-linked enzyme was then recovered by filtration, formed into particles by extrusion through a 0.8 mm screen and dried at room temperature.

For reference, the same cell sludge was cross-linked without polyazeteidine, but otherwise in the same way as above.

For comparison, the same cell sludge was immobilized by a prior-art method, viz. entrapment in polyacrylamide gel according to U.S. Pat. No. 4,248,968. More specifically, the cell sludge was diluted to 12.5% dry substance and immobilized as described in Example 12 thereof. Finally, the gel was sieved with 1 mm mesh sieve and washed with saline until the supernatant became clear.

| 11% glucose syrup | |
|---|---|
| Flow rate: | 40 g/min |
| Temperature: | 35° C. |

Pressure drop was measured after 25 hours.

5 g (dry substance) of immobilized enzyme was applied for pressure drop measurement.

| Results (pressure drop in g/cm$^2$): | |
|---|---|
| Invention | |
| cross-linking with polyazetidine | 13 |
| Reference | |
| cross-linking without polyazetidine | >200 |
| gel entrapment | >200 |

The practical effect of physical stability of a product is illustrated by the fact that a product with a pressure drop (mm liquid) of 2–4 can be used in a fixed bed column reactor with a height of 1 meter and a diameter of 1 meter with a holding time for the liquid passing therethrough of 1 minute. The packed bed may be functioning with a constant pressure drop over the bed for more than 6 months. A product with a pressure drop of more than 10 is not able to withstand these conditions.

The same situation is also seen when the process takes place in a continuous stirred tank system. Products with low grinding properties are significantly more stable in e.g. 4 m$^2$ reactor systems. Practical lifetimes of optimal products of more than 4 months can be expected without more loss than 50% activity.

We claim:

1. A process for forming polyazetidine cross-linked immobilized biologically active materials in particle form which consists essentially of:

partially cross-linking an aqueous dispersion or solution of a biologically active material with glutaraldehyde, to produce a two phase system of flocculated partially cross-linked solids containing said biologically active material and water, dewatering said two phase system and recovering the solids phase as a wet pasty mass, sub-dividing said pasty mass into discrete particles each of which is essentially homogeneous adding a polyazetidine prepolymer before, or at the beginning of partially cross-linking or subsequent thereto but prior to subdividing said pasty mass into particles, and thereafter curing said particles whereby said polyazetidine prepolymer undergoes cross-linking.

2. The process of claim 1 wherein the glutaraldehyde content in said dispersion or solution comprises 5–40% by weight of the biological material.

3. The process of claim 1 wherein said polyazetidine prepolymer is added to said aqueous dispersion prior to instituting said partial cross-linking.

4. The process of claim 3 wherein the polyazetidine is 0.5–5% w/w of total dry matter.

5. The process of claim 1 wherein said polyazetidine prepolymer is added after said partial cross-linking but prior to dewatering.

6. The process of claim 5 wherein the polyazetidine is 0.5–5% w/w of total dry matter.

7. The process of claim 1 wherein said pasty mass is mixed with aqueous prepolymer.

8. The process of claim 7 wherein the polyazetidine is 10–20% w/w dry matter basis of the biologically active material.

9. The process of claim 1 wherein water content of said particles is reduced to below about 25% by weight during the curing thereof.

10. The process of claim 1 wherein said biologically active material is an enzyme.

11. The process of claim 10 wherein said enzyme comprises enzymatically active whole, fragmented or homogenized microorganism cells.

12. The process of claim 11 wherein the microorganism is a strain from a species selected from the genus group consisting of Streptomyces, Bacillus, Actinoplanes, Fusarium, Rhodococcus, Pseudomonas and Brevibacterium.

13. The process of claim 11 wherein said enzyme comprises cell bound glucose isomerase.

14. The process of claim 10 wherein said enzyme is selected from the group consisting of glucose isomerase, penicillin acylase and nitrilase.

15. The process of claim 10 wherein said enzyme is in solution when partial cross-linking begins.

16. The process of claim 1 wherein a flocculating agent is added to said dispersion or solution before, during or after beginning said partial cross-linking, but prior to said dewatering.

17. The process of claim 1 wherein partially cross-linking said biologically active material is carried out in the presence of one or more auxiliary cross-linking agents selected from the group consisting of polyethylene imine, gelatine, albumin and carboxymethyl cellulose.

18. An immobilized enzyme product made according to the process of claim 10.

* * * * *